United States Patent
Tinkhauser et al.

(10) Patent No.: US 11,478,633 B2
(45) Date of Patent: Oct. 25, 2022

(54) METHOD AND SYSTEM FOR OPTIMISATION OF DBS PROGRAMMING

(71) Applicant: UNIVERSITÄT BERN, Bern (CH)

(72) Inventors: Gerd Tinkhauser, Bern (CH); Peter Brown, Adderbury (GB); Alek Pogosyan, Bicester (GB); Michael Schüpbach, Konolfingen (CH); Claudio Pollo, Villars-sur-Glâne (CH); Ines Debove, Bern (CH)

( * ) Notice: Subject to any disclaimer, the term of this patent is extended or adjusted under 35 U.S.C. 154(b) by 5 days.

(21) Appl. No.: 16/085,954

(22) PCT Filed: Mar. 15, 2017

(86) PCT No.: PCT/EP2017/056184
§ 371 (c)(1),
(2) Date: Sep. 17, 2018

(87) PCT Pub. No.: WO2017/158067
PCT Pub. Date: Sep. 21, 2017

(65) Prior Publication Data
US 2019/0030321 A1   Jan. 31, 2019

(30) Foreign Application Priority Data

Mar. 15, 2016 (EP) .................................. 16160544

(51) Int. Cl.
*A61N 1/05* (2006.01)
*A61N 1/36* (2006.01)
(Continued)

(52) U.S. Cl.
CPC .......... *A61N 1/0534* (2013.01); *A61B 5/0031* (2013.01); *A61B 5/2415* (2021.01);
(Continued)

(58) Field of Classification Search
CPC .............. A61N 1/0534; A61N 1/36067; A61N 1/36135; A61N 1/36182; A61N 1/36185;
(Continued)

(56) References Cited

U.S. PATENT DOCUMENTS

2011/0264165 A1* 10/2011 Molnar .............. A61N 1/36185
607/45
2014/0135870 A1* 5/2014 Carlson ................ A61N 1/0529
607/45

(Continued)

*Primary Examiner* — Erin M Piateski
(74) *Attorney, Agent, or Firm* — JMB Davis Ben-David

(57) ABSTRACT

A method and system are described for, based upon a plurality of previously-acquired directional LFP signals measured in a plurality of different directions at a directional sensor lead located in a predetermined region of a patient's brain, determining optimised patient-specific programming parameters for programming a directional stimulation lead with parameters for stimulating the said region. The method comprises a first step of determining, over at least one predetermined frequency range, a power-frequency variation curve of each of the directional LFP signals, a second step of identifying frequency peaks in the power-frequency variation curves, a third step of detecting one of the identified frequency peaks at which a maximum difference in signal power between the directional LFP signals occurs, and a fourth step of calculating a plurality of directional stimulation weighting factors on the basis of the relative signal powers of the directional LFP signals at the detected frequency peak.

13 Claims, 6 Drawing Sheets

(51) Int. Cl.
    *A61B 5/00*     (2006.01)
    *A61B 5/374*    (2021.01)
    *A61B 5/24*     (2021.01)

(52) U.S. Cl.
    CPC ............ *A61B 5/374* (2021.01); *A61B 5/4064* (2013.01); *A61B 5/4836* (2013.01); *A61B 5/7225* (2013.01); *A61N 1/36067* (2013.01); *A61N 1/36135* (2013.01); *A61N 1/36182* (2013.01); *A61N 1/36185* (2013.01)

(58) Field of Classification Search
    CPC ... A61B 5/0031; A61B 5/04002; A61B 5/048; A61B 5/4064; A61B 5/4836; A61B 5/7225
    USPC .......................................................... 607/2
    See application file for complete search history.

(56) References Cited

U.S. PATENT DOCUMENTS

2015/0351701 A1* 12/2015 Moxon ................. G16H 50/20
                                                600/544
2017/0113046 A1*  4/2017 Fried ...................... A61B 5/055
2017/0311870 A1* 11/2017 Bardakjian .......... A61B 5/4094

* cited by examiner

METHOD AND SYSTEM FOR OPTIMISATION OF DBS PROGRAMMING

FIELD OF THE INVENTION

The invention relates to the field of deep brain stimulation (DBS), which can be used for example to alleviate the symptoms of conditions such as Parkinson's Disease (PD). In particular, the invention relates to a method of determining optimised parameters for programming a stimulation regime for a directional deep brain stimulation electrode.

BACKGROUND OF THE INVENTION

Deep brain stimulation (DBS) is a proven treatment option for patients with advanced Parkinson's disease (PD), and may consist of inserting DBS leads into target cerebral regions such as the subthalamic nucleus (STN), the globus pallidus internus (GPi) or the thalamus, such that electrical current can be applied to treat disease-specific motor symptoms in patients with PD. The spatial selectivity of DBS is of the utmost importance for the quality of the clinical result; firstly, spatial selectivity helps to ensure accurate targeting of the region for therapeutic stimulation. Secondly, it helps to avoid unwanted stimulation of neighbouring structures which could result in adverse effects. It is known to use a quadripolar DBS lead with four cylindrical electrodes, also referred to as contacts, arranged in successive axial sections along its length, ie four axial sections with one electrode per axial section. Such an electrode can positioned using a known navigation technique; postoperatively, the four electrodes are tested manually by the operator to identify the electrodes which are best located in the target region. With a quadripolar electrode introduced into each of the target regions (eg right and left GPi, STN, thalamus) of both cerebral hemispheres, the procedure may typically be carried out as follows:

All the electrodes in both cerebral hemispheres are tested using different stimulation parameters, while the resulting clinical effects and side effects are assessed by interviewing the patient and by neurological examination. The patient is usually withdrawn from his/her medication before the procedure is carried out. There are four main variables that can be modified to configure the stimulation: a) the choice of active electrodes and their polarity, b) the stimulation amplitude (voltage or current), c) the frequency (Hz) and d) the pulse width (microseconds). The first electrode is selected and the stimulation amplitude (voltage or current) is slowly increased in 0.5 V (or 0.5 mA) steps, while the stimulation frequency and the pulse width remain fixed at 130 Hz and 60 µsec respectively. After resting for 2 to 5 minutes at a certain parameter configuration, the effects and side effects are determined by asking the patient and by performing a neurological examination. The stepwise increase of the stimulation amplitude is continued until limiting side effects occur. The stimulation amplitude for the best clinical effect without manifestation of limiting side effects, ie submaximal stimulation, will be documented. The same testing has to be completed for the remaining contacts and then the whole contact-testing procedure is repeated for the contralateral hemisphere. At the end of such an extended clinical contact testing, the different contacts should effectively have been ranked according to clinical effects and according to the threshold, dependent on the stimulation parameters, above which side effects appear.

However, the above prior art manual method of contact testing has the disadvantage that it takes a long time to perform (3 to 5 hours per lead), and that this lengthy, time-consuming procedure typically needs to be repeated. The procedure thus requires the involvement of specially trained neurologists and/or highly skilled specialised nurses repeatedly, over extended periods of time. The lengthy procedure is also highly fatiguing for the patient, and the results are often suboptimal due to fatiguing of the patient and prolonged withdrawal of medications with long-lasting adverse effects. Furthermore, some of the clinical effects which could be used to inform the programming decisions may not develop during the period of clinical observation for the particular selection of stimulation parameters. Erroneous decisions may be made in the selection of stimulation parameters when relying on short-term effects of stimulation only. Therefore, in many cases, stimulation effects must be reassessed again and again, often over longer periods of time, which may require inpatient admission for the subject.

As described above, therefore, the known method involves manually attempting to estimate the best configuration for symptom relief among the myriad possible different stimulation parameters. The patient's symptoms are alleviated by stimulation provided by a implanted pulse generator (IPG) and DBS electrode, programmed according to the estimation process described above. Further re-programming of the IPG may subsequently be required if the estimated parameters prove to be ineffective, and each re-programming necessitates a further clinical session for the patient.

The choice of the best-located stimulation contacts is a critical step for DBS programming in each individual patient. The manual screening procedure described above is very time-consuming for medical staff, fatiguing for the patient, and the results are often suboptimal. Consequently, this procedure must typically be repeated several times until a satisfactory parameter/contact configuration of stimulation has been identified. Unfortunately, in some patients an optimal stimulation programming is never attained, often due to lack of available expertise or time.

PRIOR ART

It has been proposed to use a directional multi-electrode DBS lead to achieve directional stimulation. A directional multi-electrode lead is known from EP2626109, for example. A simple example is shown in FIG. 1, and will be used as an illustrative example in the following description of the invention. The lead shown in FIG. 1 has eight electrodes (contacts) arranged in four axial sections similar to the sections of the quadripolar lead described above. However, the second and third axial sections of the directional electrode each comprise three contacts $3_1$, $3_2$, $3_3$ and $4_1$, $4_2$, $4_3$, formed as circumferential cylindrical surface segments, thereby allowing a different stimulation amplitude (voltage or current) to be programmed to each of three different lateral directions for each of the two mutt-contact sections. Such a directional lead permits the stimulation field to be shaped towards a desired direction within the target region, thereby allowing the DBS to be programmed with significantly greater stimulation accuracy to achieve the best clinical effect, while avoiding stimulating in directions which may induce unwanted stimulation-related side effects. However, the presence of eight stimulation contacts, with six of them stimulating in three different directions, means that the postoperative management of DBS patients, and the programming of the stimulation regime, are markedly more complicated than those of the quadripolar lead. The more electrodes on the lead, the more the manual testing of the contacts becomes time-consuming and the more the reliability of the procedure is adversely affected by patient fatigue. A lack of available expertise, infrastructure and time may be additional limiting factors impairing an appropriate manual contact testing of such a directional lead. As a consequence, the potential benefit of directional stimulation may not be fully exploited and its promise not fully realised.

A system and method are therefore needed for reducing the time taken to determine the programming parameters, and for improving their accuracy and reliability.

BRIEF DESCRIPTION OF THE INVENTION

The invention aims to overcome at least some of the above and other difficulties inherent in the prior art. In particular, the invention aims to provide a method as set out in claim 1, a system as set out in claim 12 and a computer-readable medium as set out in claim 15. Further variants of the apparatus and method of the invention are described in dependent claims 2 to 11, 13 and 14.

By systematically determining the directionality of the optimum stimulation parameters in dependence on directional local field potential (LFP) measurements, the programming parameter determining procedure can be performed a great deal more quickly, accurately and reproducibly than was hitherto possible with contact testing carried out manually by a skilled operator.

DETAILED DESCRIPTION OF THE INVENTION

The invention and its advantages will be explained in greater detail with reference to the accompanying drawings, in which.

Figure 1:
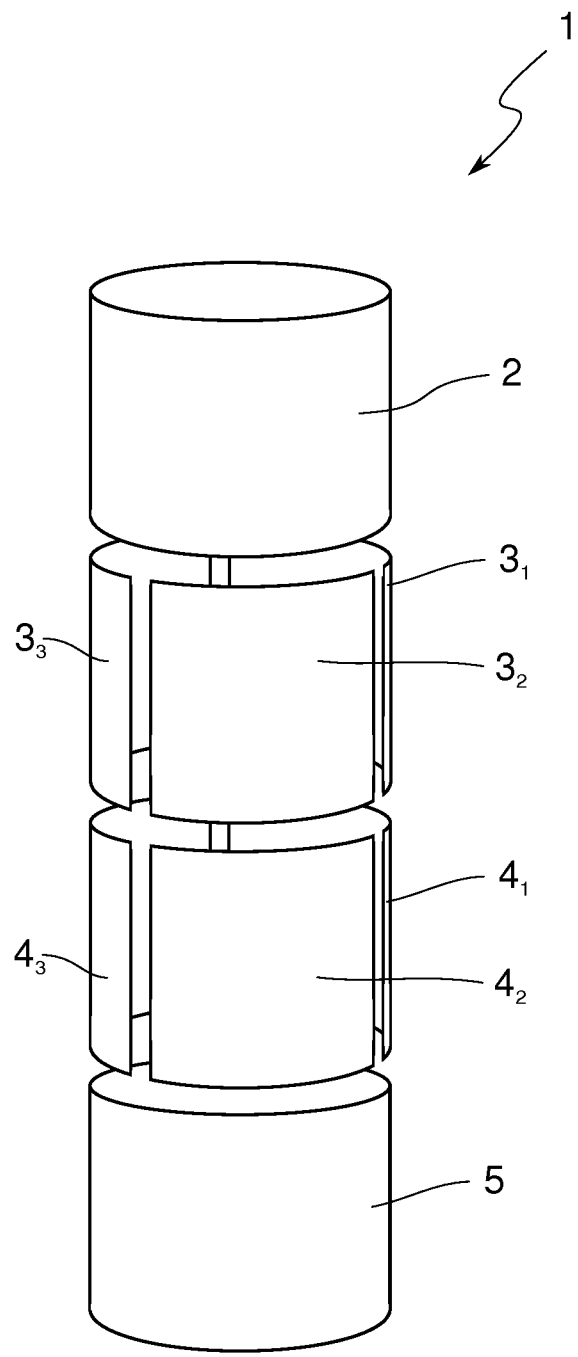
FIG. 1 shows a simplified schematic illustration of an example of a directional multi-contact DBS lead arrangement which may be used to provide LFP signal data to the method and system of the invention.

The drawings are intended merely as exemplary illustrations, for the purpose of understanding certain principles underlying the invention, and are not to be construed as limiting the scope of the invention. Where the same reference numerals are used in different drawings, these reference numerals are intended to refer to the same or corresponding features. However, the use of different reference numerals should not necessarily be taken as an indication that the referenced features differ in any particular respect.

To identify the target cerebral structure for chronic stimulation, an intraoperative recording of the neuronal activity may be performed, for example using a directional multi-contact lead such as the one shown in FIG. 1. Such a recording may reveal evidence of exaggerated oscillatory synchronisation in the STN, GPi or thalamus, which may be detected in the local field potentials (LFP). Two broad types of oscillatory activity in patients with PD have been identified: beta band activity (13-30 Hz) and gamma band activity (65-80 Hz). The power of the beta band activity without medical treatment (ie levodopa) and the degree of suppression of this activity by levodopa and DBS correlate with clinical signs of Parkinsonism (bradykinesia and rigidity) and the degree of clinical improvement with treatment, respectively. Gamma band activity, by contrast, has been shown to increase during improvement of bradykinesia and rigidity. The method and system of the invention make use of the fact that LFP signals in specific frequency bands, especially the beta band activity, are linked to the motor signs and may be used as biomarkers to optimise deep brain stimulation. LFPs recorded from directional DBS leads are screened for individual direction and depth-specific differences in the power frequency spectrum in disease-related frequency bands (eg beta band). A specific algorithm is then used to process these signal data in order to output parameters for the optimum contact configuration for programming the subsequent DBS stimulation regime. The method and system of the invention may be employed for automatic programming of the IPG connected to a directional DBS lead. Alternatively, the method and system of the invention may be employed to provide optimised programming parameters to a clinician, thereby providing a supportive tool for the clinician for programming of the IPG for the directional DBS lead.

Figure 2:
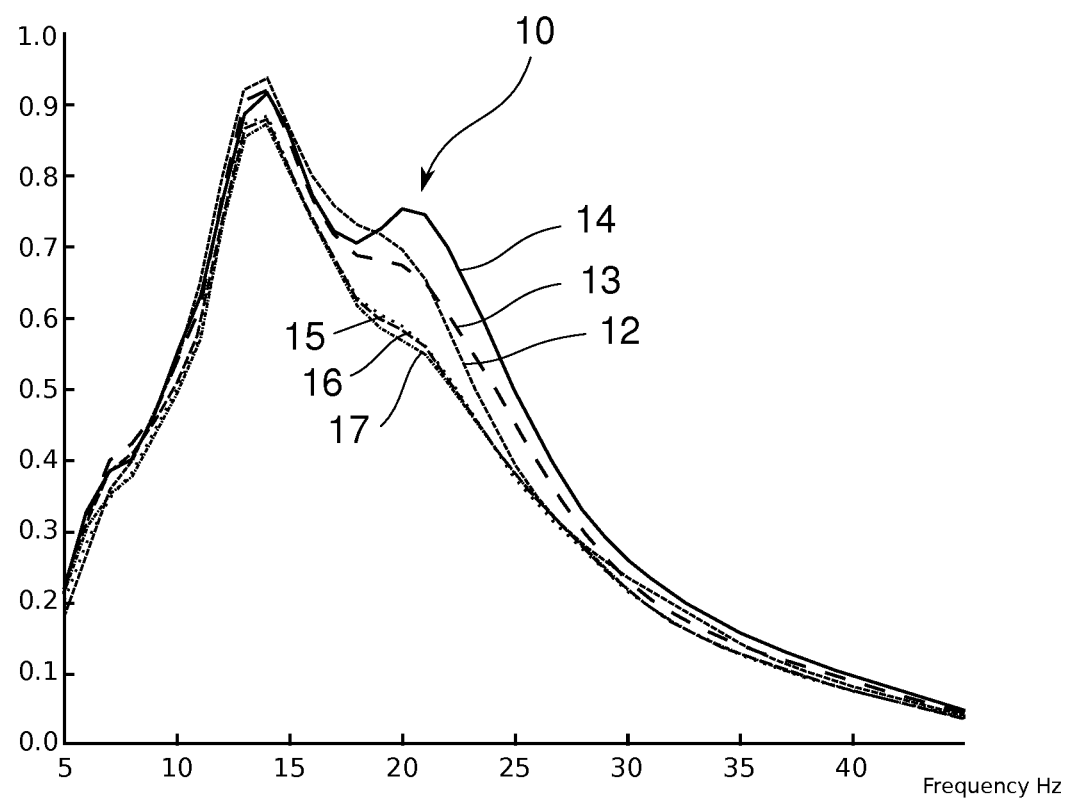
FIG. 2 shows an example of frequency-power spectra of LFP signal data acquired from the lead of FIG. 1 for a particular DBS site of a particular patient.

FIG. 2 shows an example set of frequency-power spectra of LPF signal data acquired from the lead 1 of FIG. 1, for a particular DBS site of a particular patient. Curves 12, 13, 14, 15, 16, and 17 show the spectra of the LFP signal data acquired in the beta band from contacts $3_1$, $3_2$, $3_3$, $4_1$, $4_2$ and $4_3$ respectively. A local peak 10 can be seen in the curve 14 for contact $4_3$ at approximately 20 Hz. As will be described below, this peak 10 can be detected using an algorithm for detecting peaks in each spectral power curve and determining at which of the peaks the difference between the amplitudes (ie the spread of the amplitude values) among one set of directional contacts (ie $3_1$, $3_2$ and $3_3$ or $4_1$, $4_2$ and $4_3$) are greatest. As will be described below, this maximum difference calculation may be based on normalized and/or baseline-corrected values of the frequency curves within a frequency window (referred to as the DIFR) at the peak under consideration. Signal differences and signal comparability can be improved by carrying out normalization and/or baseline correction steps in order to increase the signal-to-noise ratio. Normalization steps may include various spectral components, and may involve for example contrasting the peak amplitude with the mean amplitude of the whole disease-related frequency band.

Note that the example given in this description assumes that the geometrical arrangement of the sensor lead contacts corresponds directly to that of the stimulation lead, however this need not necessarily be the case. Stimulation weightings may be mapped using appropriate transformation from the geometric configuration of the directional sensor(s) to the geometric configuration of the directional stimulation electrode(s).

Similarly, the method steps are described in the context of monopolar measurements (ie assessing each contact separately, with a common reference). In the monopolar method, power frequency curves are derived for each contact, and the magnitude of the disease-related spectral component is ranked for the contacts individually. However, it should be understood that the same techniques may be applied to more than single contact at once, in a bipolar or multipolar fashion, such that so-called "montages" or arrangements of multiple contacts may be assessed and ranked. Method steps applied to individual contacts in this description should be understood to encompass the application of the steps to montages of two or more contacts. Determining the magnitude of the disease-related spectral components in such a group-wise, combinatorial fashion greatly increases the number of possible choices to be ranked, and improves the signal-to-noise ratio of the derived results (power frequency curves and detected peaks).

Figure 3A:
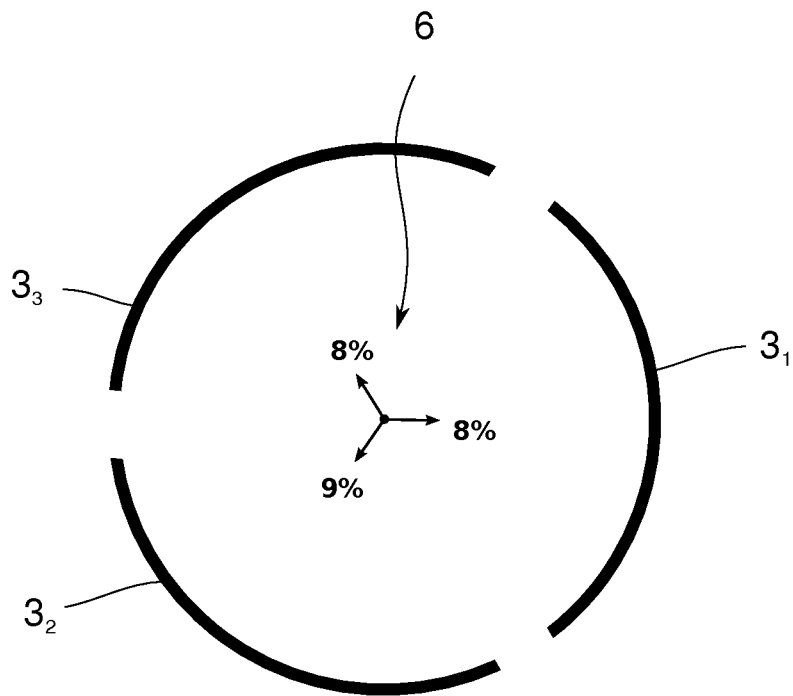
FIGS. 3a and 3b show schematic graphical representations of DBS directional weightings which may be determined by the inventive method and system from the signal data of FIG. 2.
Figure 3B:
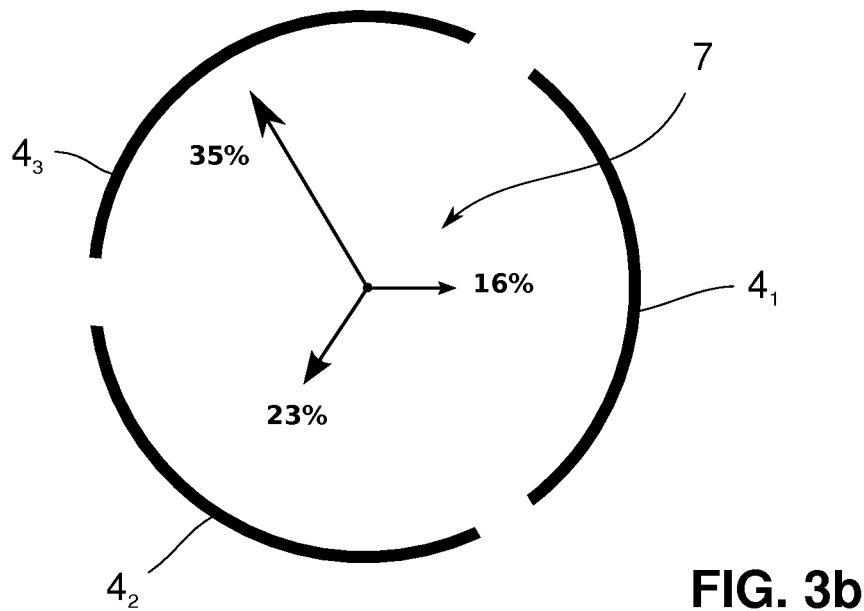

FIGS. 3a and 3b show how the spectral power curves of FIG. 2 may be used to derive directional weightings 6 and 7 for the stimulation amplitudes at contacts $3_1$, $3_2$ and $3_3$ (FIG. 3a) and contacts $4_1$, $4_2$ and $4_3$ (FIG. 3b). In FIG. 3a, the three electrodes $3_1$, $3_2$ and $3_3$ show almost zero directional weighting (8%, 9% and 8% respectively), whereas FIG. 3b shows that the three electrodes $4_1$, $4_2$ and $4_3$ are markedly weighted (16%, 23% and 35% respectively). In this example, the inventive method predicts that the DBS should be weighted in favour of the contact $4_3$ in order to achieve optimum targeting of the structure to be stimulated. A manual contact testing was carried out blind on the patient whose LFP signals were recorded to generate the spectral curves of FIG. 2, and the manual contact testing produced the following recommended directional stimulation currents for each of the directional contacts of the DBS lead of FIG. 1 as follows:

$3_1$: 4.0 mA
$3_2$: 3.5 mA
$3_3$: 3.0 mA
$4_1$: 2.5 mA
$4_2$: 2.5 mA
$4_3$: 2.0 mA

As can be seen from the above, the manual contact testing approach confirmed the prediction, made by the method of the invention, that contact $4_3$ would provide the best result (lowest stimulation current for effective symptom relief). However, the manual contact testing took six hours of intensive, fatiguing clinical work, while the recommendation from the inventive method was delivered almost instantly.

Note that the graphical representation of FIGS. 3a and 3b are examples of how the directional contact weighting may be presented graphically to a clinician so that he or she may adjust the DBS programming accordingly. Alternatively, the calculated weightings may be used directly in an automated programming of the IPG and DBS electrode.

Figure 4:
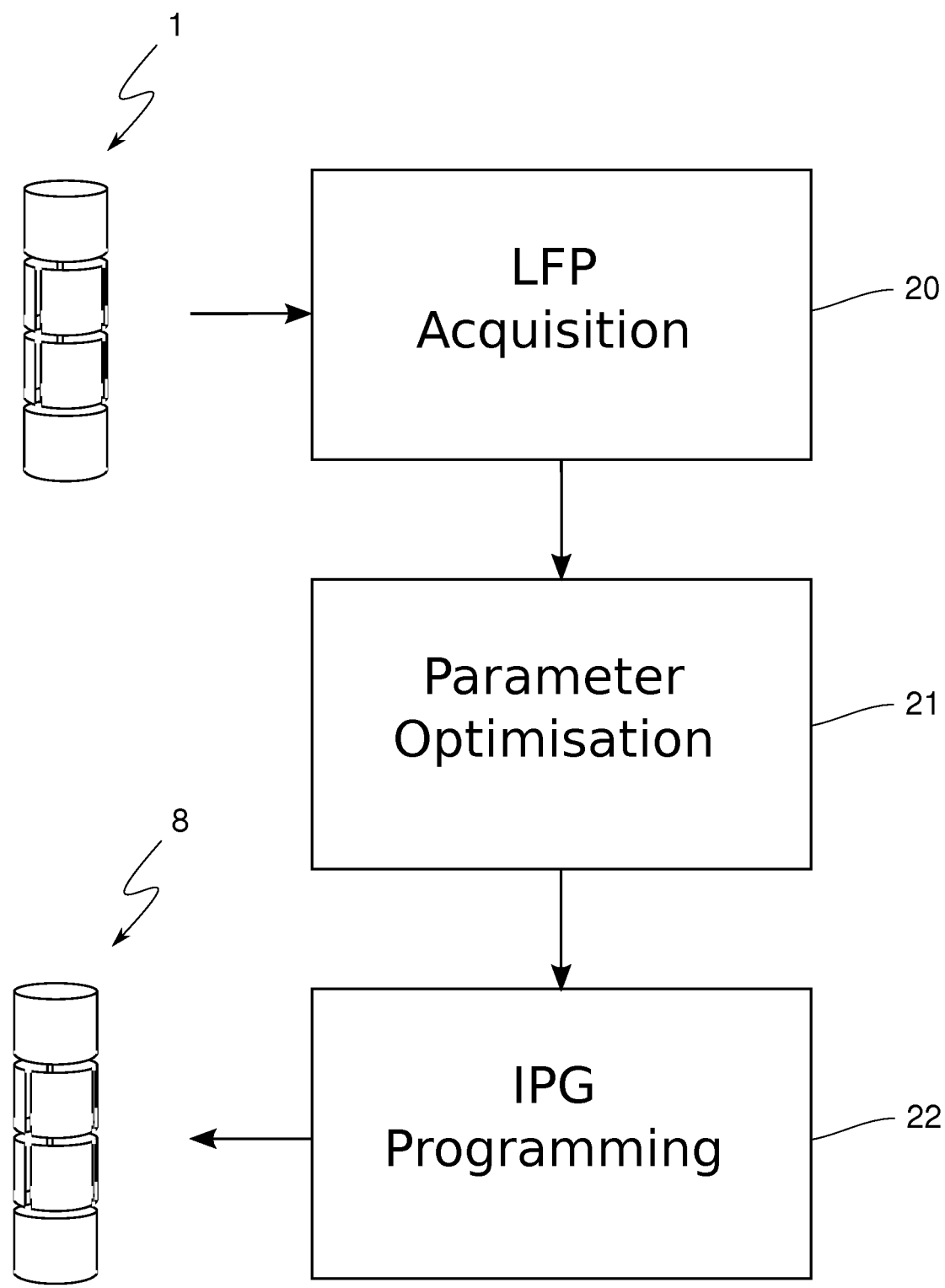
FIG. 4 shows a simplified top-level abstraction of an example of a clinical procedure incorporating the method of the invention.

FIG. 4 shows an overview of the context of the method and system of the invention in the overall DBS process. In step 20, directional LFP signals are acquired from directional sensing electrode 1, such as the lead shown in FIG. 1. The acquired signals are processed in step 21, using to a method according to the invention, to generate directionally optimised programming parameters which are then used in step 22 to program an IPG driving a directional DBS lead 8 (which may typically be the lead 1, ie the DBS lead serves as sensor and stimulation lead).

The LFP signal acquisition step 20 may comprise recording LFPs from the directional lead after its placement in the definitive position within the target structure (eg STN, GPi or thalamus). During the recording, the patient must be withdrawn from dopaminergic medication, the patient must be awake and in a resting position without any voluntary movement. Recording can be performed intraoperatively or postoperatively before the electrode is connected to the implantable pulse generator (IPG). Alternatively, LFPs can be recorded at any time point from the IPG itself, if the IPG is capable of LFP recording.

Figure 5:
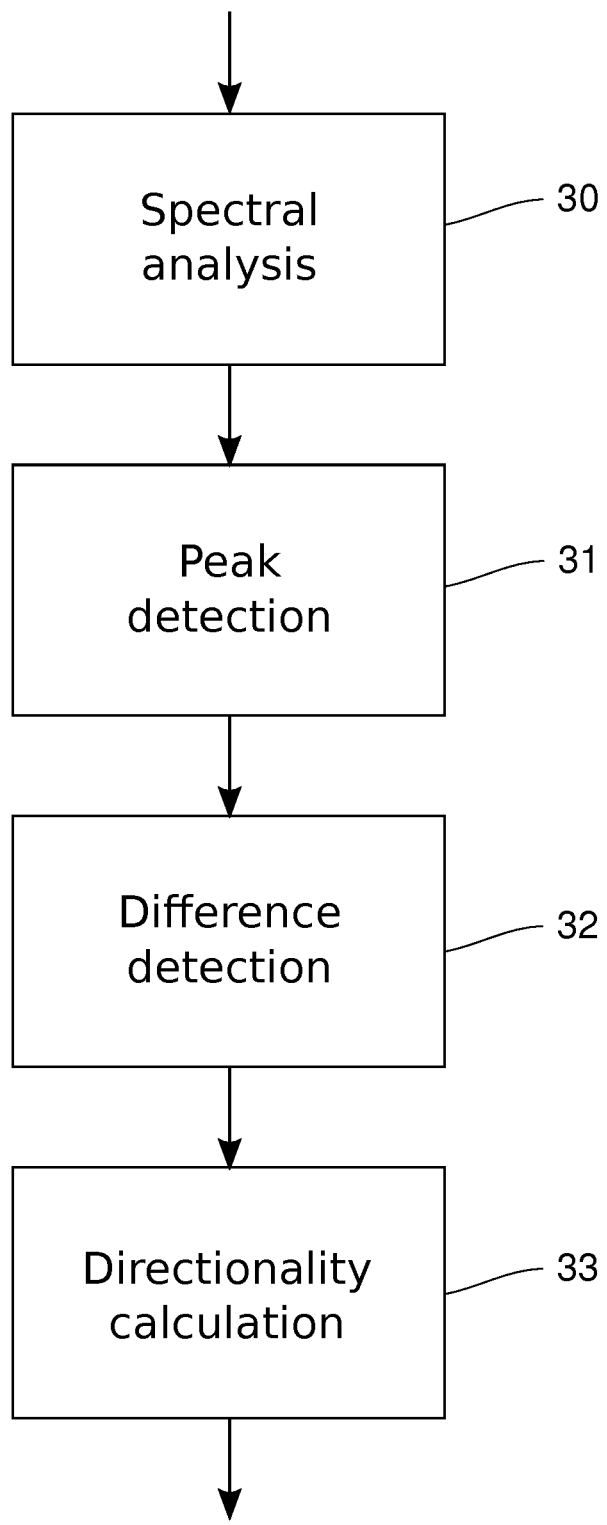
FIG. 5 shows a more detailed view of the steps carried out in a method according to the invention.

The method steps underlying step 21 of FIG. 4 are described below, with particular reference to FIGS. 5 and 6. As described above, the method of the invention comprises the steps of spectral analysis 30 of the LFP signal data in order to generate spectral power curves for each directional electrode on the sensor lead 1;

peak detection 31 to identify any local peaks in each of the spectral power curves;

difference detection 32 for determining the peak at which there is the greatest difference in amplitude among the directional electrodes of a section of the lead; and directionality calculation 33, for deriving weightings for stimulation signals applied to each of the directional electrodes of the DBS lead 8.

Figure 6:
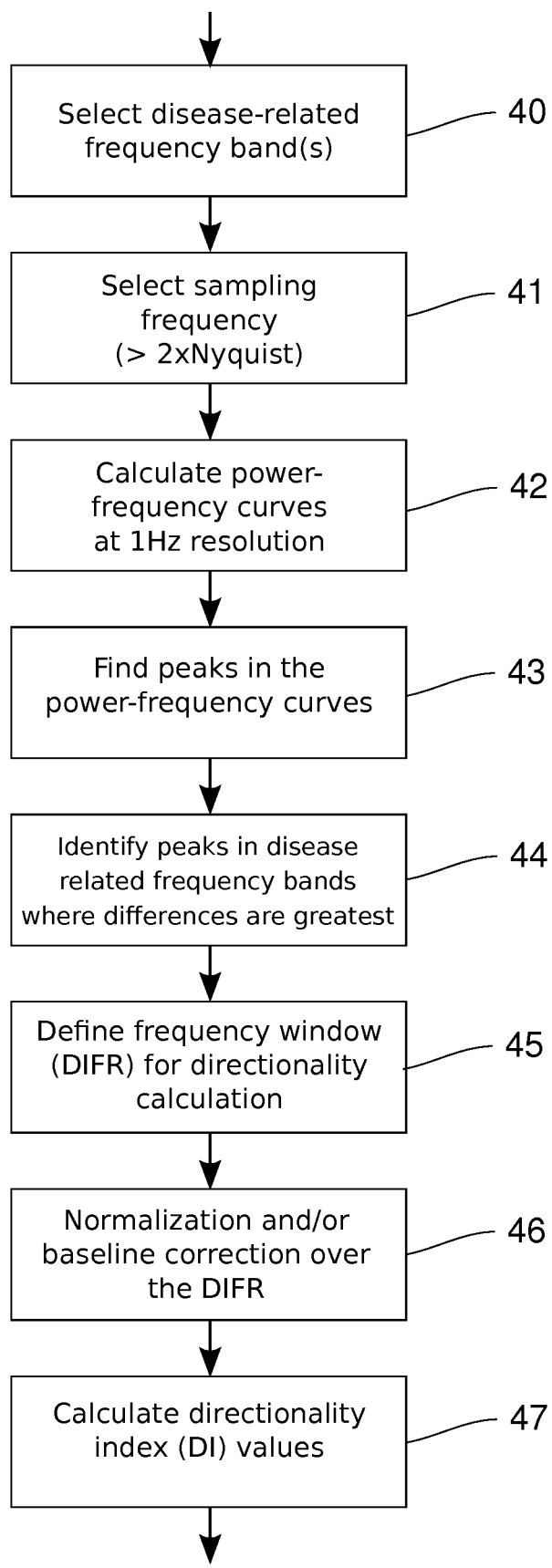
FIG. 6 shows in even greater detail the steps and substeps which may be carried out in a method according to the invention.

FIG. 6 shows an example flow diagram of a method according to the invention. In step 40, one or more suitable frequency bands are selected, according to current knowledge, for analysing the LFP signals associated with a particular disease. The frequency band(s) may advantageously comprise the beta frequency range (13-35 Hz). In principle, several frequency bands present in the LFP may be used as biomarkers (alone or in combination) to guide stimulation, however on the premise of an existing relationship to the disease. Such a relationship could be positive (associated with symptom alleviation) or negative (associated with symptom deterioration). In step 41, a suitable sampling frequency is determined for the subsequent spectral analysis, the sampling frequency being preferably at least twice the Nyquist limit for the LFP signal data. In step 42, the power-frequency-spectrum (spectral analysis with frequency decomposition) for each directional contact is calculated, at eg 1 Hz resolution. In step 43, local peaks in the power-frequency curves are identified. Within the disease-related frequency band, the frequency peak showing the largest differences among directional contacts is identified in step 44. In step 45, this peak frequency is transformed into a frequency range (DIFR) by adding and subtracting a predetermined spectral bandwidth, such as 3 Hz, to give a total width of 7 Hz. The width of DIFR (eg peak frequency±3 Hz) can be set to maximize directional information between the contacts. The width of the DFIR may be predetermined, or it may be dynamically adapted, for example in dependence on a characteristic of the power-frequency curves. In step 46, the average amplitude for each directional contact over the DIFR is baseline corrected by subtracting 90% of the mean amplitude of the directional contact with the lowest amplitude in the DFIR. This step helps to reduce the effect of volume conduction and to improve the visualisation of the spectral differences between the contacts. The baseline corrected average amplitudes for each contact are then summed in step 47, and percentage distribution over the directional contacts is calculated to determine a directionality index (DI). The DI of each directional contact allows contacts to be ranked according to the likelihood that they will afford the best clinical response on stimulation, which is defined as the lowest stimulation intensity required for sufficient clinical response. The percentage value itself does not indicate a percentage clinical response. Where two or more of the directional contacts in a particular lead section have similar DI values, they may be considered in combination for stimulation. The directionality index is superimposed graphically as a vector and as percentage value for each directional contact on a visual model illustrating the stimulation contacts and contact levels. This enables the clinician to immediately understand which section and which directional contact are likely to produce the best DBS results.

The parameters determined in the method described above may be exported (manually or automatically) into the IPG which drives the DBS stimulation device. The clinician should therefore start to deliver the stimulation on the contact with the highest directionality index, adjusting other stimulation parameters (current, frequency, pulse width etc) accordingly and, if necessary, move on to a different contact, or a different combination of contacts, suggested by the directionality index results if the stimulation effect is clinically not sufficient or if side effects occur. In IPGs with LFP recording capabilities and integrated analysis modules, the inventive method, and the system which embodies it could be fully integrated and automated as an internal feature of the IPG.

The method described above may preferably be implemented as instructions stored on non-transitory computer-readable media, and/or in a system comprising one or more specially configured or programmed electronic circuits.

I claim:

1. A method comprising using at least one hardware processor for determining patient-specific optimized programming parameters to facilitate programming a directional multi-electrode stimulation lead with parameters for stimulating a region based upon a plurality of directional local field potential ("LFP") signals measured in a plurality of different directions by a sensor located in a predetermined region of a patient's brain, said processor configured to: determine, over at least one predetermined frequency ranges, a power-frequency variation curve for each directional LFP signal recorded from the at least one sensor of at least one deep brain stimulation ("DBS") lead; identify, through a spectral analysis calculation, at least one frequency peak in said power-frequency variation curve; detect one of said at least one identified frequency peaks at which a maximum difference in signal power between the directional LFP signals occurs; calculate a plurality of directionally weighted stimulation indices for the directional multi-electrode stimulation lead on the basis of the relative signal powers of the directional LFP signals at the frequency of the detected frequency peak; and automatically selecting an electrode configuration on the directional multi-electrodes stimulation lead connected to an implanted pulse generator to facilitate optimization of a subsequent DBS regime.

2. The method of claim 1, wherein the frequency range comprises a beta frequency range.

3. The method of claim 1, wherein determining the power-frequency variation curve comprises determining power-frequency curves for a plurality of frequency ranges, the frequency ranges being usable alone or in combination to guide stimulation.

4. The method of claim 1, wherein calculating the plurality of directionally weighted stimulation indices comprises:
selecting a directionality indicating frequency range ("DIFR") based on the detected frequency peak; and
determining a directionality index ("DI") for each electrode of a plurality of electrodes of said directional stimulation lead and for each montage of the plurality of montages of said electrodes of said directional stimulation lead.

5. The method of claim 4, wherein said DIFR is a predetermined constant frequency range centered on the frequency of the detected frequency peak, wherein the width of said DIFR is selected in dependence on the frequency of said detected frequency peak.

6. The method of claim 4, wherein determining the directionality index comprises normalizing a baseline correction of an average amplitude of each of said power-frequency variation curves in said DIFR.

7. The method of claim 6, wherein said baseline correction comprises subtracting a predetermined proportion of the average amplitude from an amplitude of each of the curves.

8. The method of claim 7, further comprising summing an average amplitude of each curve over said DIFR to give a proportional distribution for each direction associated with each of the curves.

9. A system comprising at least one hardware processor configured to determine optimized patient-specific electrode configuration to facilitate programming of a directional multi-electrode stimulation lead, having a directional sensor and stimulation electrodes, for stimulating a predetermined region of a patient's brain, said processor configured to receive a plurality of previously-acquired directional LFP signals measured in a plurality of different directions by the directional sensor lead configured to be located in the predetermined region of the patient's brain; determine, through a spectral analysis calculation, over at least one predetermined frequency range, a power-frequency variation curve for each of the directional LFP signals; identify, through peak detection, at least one frequency peak in the power-frequency variation curves determined by the spectral analysis calculation means; detecting one of the at least one identified frequency peaks at which a maximum difference in signal power between the directional LFP signals occurs; calculate, through a directionality determination, a plurality of directionally weighted stimulation parameters for the directional stimulation lead on the basis of relative signal powers of the directional UP signals at a frequency of the detected frequency peak; and automatically configure an electrode combination on the directional multi-electrodes stimulation lead connected to an implanted pulse generator to facilitate optimization of a subsequent DBS regime.

10. The system of claim 9, further comprising an implantable pulse generator device, wherein at least one of the spectral analysis calculations, peak detection, difference detection, and directionality determination are integrated into the pulse generator device for driving the directional multi-electrodes stimulation lead.

11. The system of claim 9, further comprising a directional multi-electrodes stimulation lead configured to perform directional stimulation according to directionally weighted stimulation parameters provided by said processor.

12. The system of claim 9, further comprising a programmable implantable pulse generator device for driving said directional multi-electrodes stimulation lead, wherein the said programmable implantable pulse generator device for is configured to acquire and record LFP signal data from said sensor lead.

13. A computer program product for determining optimized patient-specific programming parameters to facilitate programming a directional multi-electrode stimulation lead with parameters for stimulating the region based upon a plurality of directional low field potential ("LFP") signals measured in a plurality of different directions at a directional sensor configured to be located in a predetermined region of a patient's brain, the computer program product comprising a non-transitory computer-readable storage medium having program code embodied therewith, the program code executable by at least one hardware processor to: determine, over at least one predetermined frequency range, a power-frequency variation curve for each directional LFP signal of the directional LFP signals recorded from directional multi-electrodes stimulation lead; identify, through a spectral analysis calculation, at least one frequency peak in the said power-frequency variation curves; detect one of said at least one identified frequency peaks at which a maximum difference in signal power between the directional ITP signals occurs: calculate a plurality of directionally weighted stimulation indices for the directional stimulation lead on the basis of relative signal power of the directional LFP signals at the frequency of the detected frequency peak: and automatically selecting an electrode configuration on the directional multi-electrodes stimulation lead connected to an implanted pulse generator to facilitate optimization of a subsequent DBS regime.

* * * * *